United States Patent
Lee et al.

(10) Patent No.: US 9,133,229 B2
(45) Date of Patent: Sep. 15, 2015

(54) ECONOMIC PROCESS FOR PRODUCING XYLOSE FROM HYDROLYSATE USING ELECTRODIALYSIS AND DIRECT RECOVERY METHOD

(75) Inventors: Joo-hang Lee, Gyeonggi-do (KR); Jun-gap An, Gyeonggi-do (KR); Seung-won Park, Gyeonggi-do (KR); Taek-beom Kim, Seoul (KR); Seong-bo Kim, Seoul (KR); Dong-hoon Lee, Gyeonggi-do (KR); Woon-hwa Lee, Seoul (KR); Dae-Ho Son, Incheon (KR); Seung-bae Ji, Incheon (KR); Kang-pyo Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 520 days.

(21) Appl. No.: 13/503,221

(22) PCT Filed: Oct. 30, 2009

(86) PCT No.: PCT/KR2009/006359
§ 371 (c)(1),
(2), (4) Date: Apr. 20, 2012

(87) PCT Pub. No.: WO2011/052824
PCT Pub. Date: May 5, 2011

(65) Prior Publication Data
US 2012/0211366 A1    Aug. 23, 2012

(51) Int. Cl.
*B01D 61/44* (2006.01)
*C07H 3/02* (2006.01)
(Continued)

(52) U.S. Cl.
CPC .............. *C07H 3/02* (2013.01); *B01D 61/422* (2013.01); *C13B 20/165* (2013.01); *C13K 13/002* (2013.01)

(58) Field of Classification Search
USPC .......................................... 204/530; 435/105
See application file for complete search history.

(56) References Cited

U.S. PATENT DOCUMENTS

| 3,718,560 A | 2/1973 | Sugiyama et al. |
| 4,612,286 A | 9/1986 | Sherman et al. |

(Continued)

FOREIGN PATENT DOCUMENTS

| CN | 1165195 A | 11/1997 |
| CN | 1298413 A | 6/2001 |

(Continued)

OTHER PUBLICATIONS

Daud et al. (2000) Carbon. 38:1925-1932, "The effects of carbonization temperature on pore development in palm-shell-based activated carbon".

(Continued)

*Primary Examiner* — Arun S Phasge
(74) *Attorney, Agent, or Firm* — Swanson & Bratschun, L.L.C.

(57) ABSTRACT

The present invention relates to an environmentally friendly, simple and economic process for producing xylose. The process comprises the steps of: a) countercurrently extracting tropical fruit biomass by hydrolysis with sulfuric acid to obtain a high-concentration xylose extract; b) adjusting the extract to a pH of 1.5-2.5 and decolorizing and filtering the pH-adjusted extract; c) desalting the filtrate in an electrodialysis device; and d) recycling a waste sulfuric acid solution recovered from step c), to step a), and concentrating and directly recovering the desalted filtrate to obtain xylose crystals.

5 Claims, 3 Drawing Sheets

(51) Int. Cl.
*C13B 20/16* (2011.01)
*C13K 13/00* (2006.01)
*B01D 61/42* (2006.01)

(56) References Cited

U.S. PATENT DOCUMENTS

| | | | |
|---|---|---|---|
| 4,668,340 A * | 5/1987 | Sherman | 162/16 |
| 4,778,531 A | 10/1988 | Dobler et al. | |
| 5,340,403 A | 8/1994 | Fields et al. | |
| 6,352,845 B1 | 3/2002 | Buchanan et al. | |
| 6,663,780 B2 | 12/2003 | Heikkila et al. | |
| 7,008,485 B2 | 3/2006 | Heikkila et al. | |
| 7,109,005 B2 | 9/2006 | Eroma et al. | |
| 8,283,139 B2 | 10/2012 | Park et al. | |
| 2002/0153317 A1 | 10/2002 | Heikkila et al. | |
| 2006/0281913 A1 | 12/2006 | Ferreria et al. | |
| 2010/0068121 A1 * | 3/2010 | Park et al. | 423/445 R |

FOREIGN PATENT DOCUMENTS

| | | |
|---|---|---|
| CN | 1861520 A | 11/2006 |
| JP | 54-067093 | 5/1979 |
| JP | B 1981-039638 | 9/1981 |
| JP | A 1984-179099 | 10/1984 |
| JP | A 1991-232500 | 10/1991 |
| JP | A 1992-197192 | 7/1992 |
| JP | H10-192000 A | 7/1998 |
| JP | H11-313700 A | 11/1999 |
| JP | 2001-226111 | 8/2001 |
| JP | A 2005-229821 | 9/2005 |
| JP | 2006-087390 A | 4/2006 |
| JP | 2006-238728 | 9/2006 |
| JP | A 2006-238728 | 9/2006 |
| JP | A 2009-520504 | 5/2009 |
| KR | 10-2000-012825 A | 3/2000 |
| KR | 10-2000-038423 A | 7/2000 |
| KR | 10-2000-051095 A | 8/2000 |
| KR | 10-2000-055003 A | 9/2000 |
| KR | 10-2001-0107331 | 12/2001 |
| KR | 10-2002-0059673 | 7/2002 |
| KR | 10-2002-0095809 A | 12/2002 |
| KR | 10-2004-0008121 | 1/2004 |
| KR | 2004-18323 A | 3/2004 |
| KR | 10-2005-003585 A | 1/2005 |
| KR | 10-2005-0025059 A | 3/2005 |
| KR | 10-2005-0031310 A | 4/2005 |
| KR | 10-2005-0071400 | 7/2005 |
| KR | 10-2008-0074687 | 8/2008 |
| WO | WO 02/053783 | 7/2002 |
| WO | WO2008/096971 A1 | 8/2008 |

OTHER PUBLICATIONS

Daud & Ali (2004) Bioresource Technology. 93:63-69, "Comparison on pore development of activated carbon produced from palm shell and coconut shell".

Demirbas (2006) J. Anal. Appln. Pyrolysis 76:285-289, "Effect of temperature pyrolysis products from four nut shells".

Huang et al. (2005) Institute of Science and Engineering, Hainan University, Fine Chemical Industry Key Laboratory of Hainan, Hikou 570228, China 26(8):252-255, "The Choice of the Best Technology in the Xylose Solution Prepared Xylose by the Coconut Shell".

Internet publication: www.knrda.go.kr/club/club_beta/05/sub-04-main3-199.htm, (2002) "Process and use of starch" (w/ English abstract).

Parajo et al. (1998) "Production of Carotenoids by Phaffiarhodozyma Growing on Media Made from Hemicellulosic Hydrolysates of Eucalyptus globulus Wood" Biotechnology and Bioengineering, 59(4):501-506.

Roehr (2001) "Classical and Future Applications, Wiley-VCH" Biotechnology of Ethanol, 173-173.

Search Report issued Apr. 7, 2008 in PCT/KR2008/000457.

Shibanuma (1999) "Partial Acid Hydrolysis of Corn Fiber for the Production of L-Arabinose" J. Appl. Glycosci, 46(3):249-256.

Written Opinion issued Apr. 7, 2008 in PCT/KR2008/000457.

EP Search Report issued Nov. 27, 2013 in EP 09850895.5.

International Search Report for PCT/KR2009/006359 dated Aug. 16, 2010 (English Translation).

* cited by examiner

ECONOMIC PROCESS FOR PRODUCING XYLOSE FROM HYDROLYSATE USING ELECTRODIALYSIS AND DIRECT RECOVERY METHOD

CROSS-REFERENCE TO RELATED APPLICATION

The present invention is a national phase entry under 35 U.S.C. 371 of international application No. PCT/KR2009/006359 filed on Oct. 30, 2009. The disclosures of said application are incorporated by reference herein.

TECHNICAL FIELD

The present invention relates to an economic process for producing xylose which is not only environmentally friendly by eliminating the processes that generate large amounts of wastewater such as neutralization and ion purification processes, but also cost-saving by simplifying the processes

BACKGROUND ART

To purify useful sugar components containing xylose from sulfuric acid hydrolysates, precipitation and processes of ion exchanges have been most frequently used. Among them, the ion-exchange method has been frequently used commercially, because it has low equipment costs and has been conventionally used. However, a large amount of wastewater containing a high concentration of salts is generated during regeneration of ion exchange resin, thus increasing wastewater treatment costs. For this reason, alternative technology capable of reducing the chemical substances usage and the amount of wastewater is required.

Recently, new separation technology such as electrodialysis has been reported as a desalting method of molasses and fermentation broth to use resources effectively. Korean Patent Laid-Open Publication No. 2008-0074687 discloses a method of producing xylose from tropical fruit biomass via hydrolysis, neutralization, precipitation, filtration, electrodialysis and ion-exchange steps. The bottleneck of electrodialysis process is that the ion-exchange membrane is easily contaminated by organic compounds. It is well known that this contamination reduces the efficiency of the device and shortens the life cycle of the membrane.

In order to solve this problem, pretreatment with a water softener or an anion exchange resin was attempted (Japanese Patent Laid-Open Publication No. Sho 54-67093). However, there is a limit to industrial application of this method because it has a problem that the costs rise up as several pretreatment steps and sub-materials are needed. Korean Patent Laid-Open Publication No. 2001-0107331 about a method of recovering lactic acid by an electrodialysis discloses a process of recycling ammonium sulfate and advantages such as efficiency and environmental advantages. However, electrodialysis still has a problems associated with the cost of membranes, the contamination of membranes and the stability of long-term operation, when it is industrially applied.

DISCLOSURE

Technical Problem

The present inventors have conducted extensive studies to solve the above mentioned problems occurring in the prior art. As a result, they have found that a decrease in productivity caused by the contamination of an ion exchange membrane can be prevented by providing the range of pH that can avoid scaling which causes the contamination of the ion exchange membrane, whereby the limitation of industrial application of electrodialysis can be overcome by eliminating expenses such as enormous initial investment and operational cost. In addition, the present inventors have found that an ion-exchange process can be eliminated by a direct recovery process that maximizes the purity of extraction. Therefore, a burden of wastewater treatment containing a high concentration of salts can be eliminated, thereby completing a simple process for producing xylose.

Accordingly, main purpose of the present invention is to provide a process in which xylose is extracted as much as possible from tropical fruit biomass via countercurrent extraction, while sulfuric acid ions are selectively separated, recovered and recycled to the extraction process that gives targeted organic material can be recovered directly as crystals.

Also, an electrodialysis device can be operated for a long period of time without chemical cleaning by preventing the contamination of the ion exchange membrane.

Technical Solution

In order to accomplish the above object, the present invention provides a process for producing xylose, comprising the steps of: a) countercurrently extracting tropical fruit biomass by hydrolysis with sulfuric acid to obtain a high-concentration xylose extract; b) adjusting the extract to a pH of 1.5-2.5 and decoloring and filtering the pH-adjusted extract; c) desalting the filtrate in an electrodialysis device; and d) recycling a waste sulfuric acid solution recovered from step c), to step a), and then concentrating the desalted filtrate and directly recovering the organic material to obtain xylose crystals.

Advantageous Effects

When xylose is produced using an electrodialysis device and a direct recovery process method of the present invention, a burden for wastewater treatment can be reduced and the production cost also can be reduced by simplification of process. Thus, the present invention can provide a low-pollution process for producing xylose, which can reduce raw material costs and contribute to the prevention of environmental pollution.

BEST MODE

The present invention provides a process for producing xylose, comprising the steps of: a) countercurrently extracting tropical fruit biomass by hydrolysis with sulfuric acid to obtain a high-concentration xylose extract; b) adjusting the extract to a pH of 1.5-2.5 and decoloring and filtering the pH-adjusted extract; c) desalting the filtrate in an electrodialysis device; and d) recycling a waste sulfuric acid solution recovered from step c), to step a), and concentrating the desalted filtrate and directly recovering the organic material without additional ion purification and decoloration, to obtaining xylose crystals.

Figure 1:
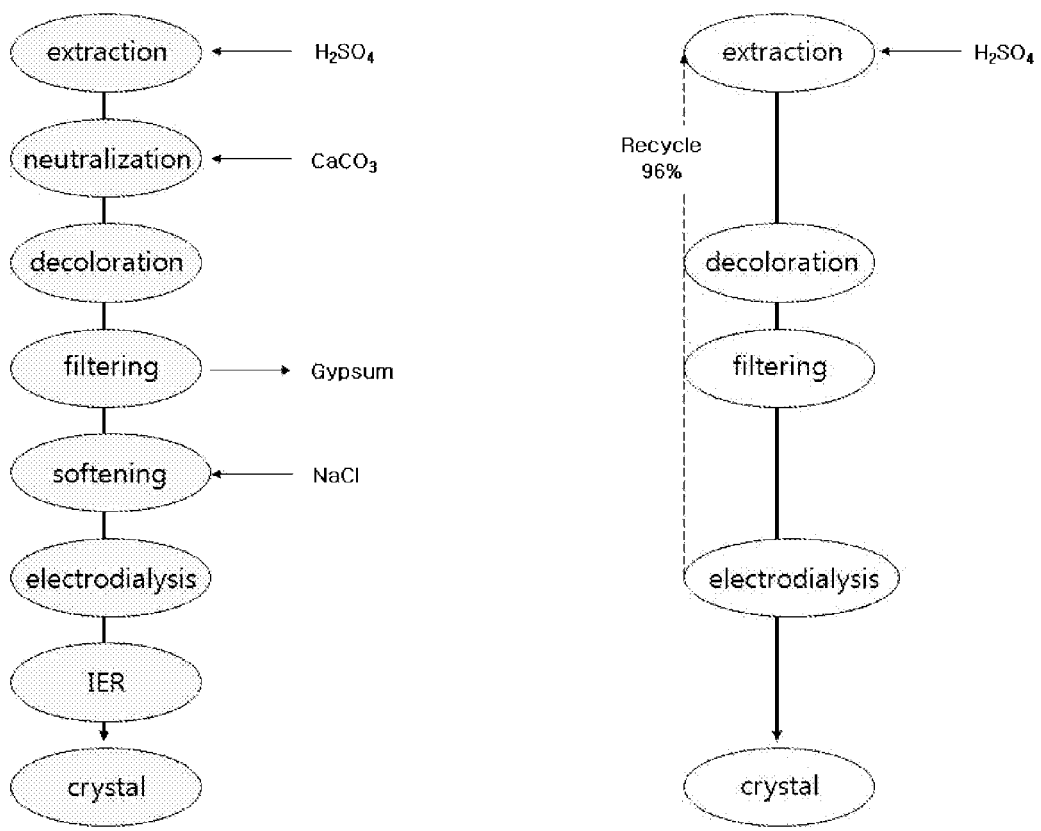
FIG. 1 shows a comparison between a flow diagram of a process of producing xylose using neutralization, ion exchange and electrodialysis according to the prior art and a flow diagram of a simplified process of producing xylose using electroldialysis and direct recovery process according to the present invention.
Figure 2:
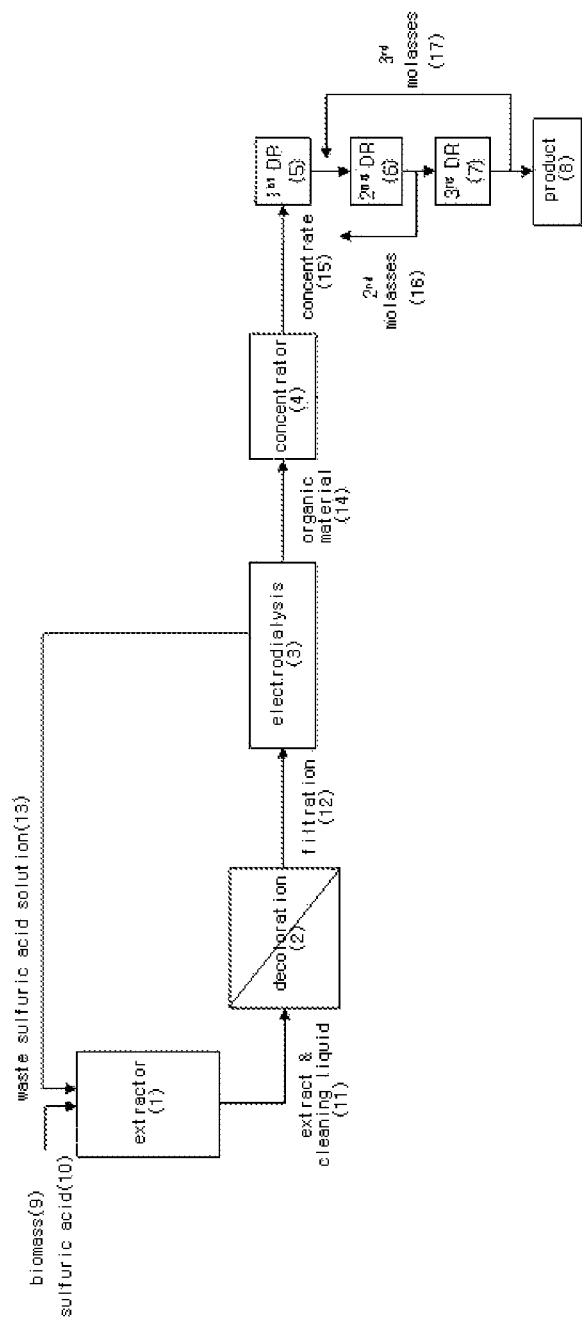
FIG. 2 shows a detailed diagram of the inventive process of producing xylose by separating an organic material and sulfuric acid by an electrodialysis process and recycling the recovered sulfuric acid while directly crystallizing the organic material.

The process for producing xylose of the present invention is shown in FIG. 2 and will now be described in detail with reference to the accompanying drawings.

Referring to FIG. 2, a tropical fruit biomass (9) can be a dried coconut shell, a palm shell or an oil palm empty fruit bunch (OPEFB).

The hydrolysis in the process of the present invention can be carried out by adding 2,000-50,000 ppm of a sulfuric acid solution (10) to the tropical fruit biomass (9) and allowing the mixture to react at a temperature of 100-200° C., reaction pressure of 0-10 kgf/cm$^2$ for 0.5-10 hours.

Extraction of the tropical fruit biomass is carried out under the above hydrolysis conditions, and countercurrent extraction can be performed using an extractor (1) shown in FIG. 2.

The sugar contents ratio of an extract (11) obtained by the countercurrent extraction is 60-90%, and preferably 80-90%, based on the weight of the separated mixed hydrolysates.

The extract (11) is decolorized using activated carbon and is filtered through a filter press or ultrafiltration device (2) to remove suspended materials. In one embodiment of the present invention, the filter press or the ultrafiltration device comprises a filter cloth having a pore size of 0.5 µm.

A filtrate (12) from which the suspended material has been removed is adjusted to a pH of 1.5-2.5. This pH adjustment is carried out in order to prevent a scale formed in the hydrolysate containing proteins, pigments and humic substances which are contaminate the electrodialysis membrane.

A waste sulfuric acid solution recovered from step c) (13) can be recycled to extraction step a) so that it can be continuously reused in the next extraction process. The recovered sulfuric acid solution can be reused after adding sulfuric acid up to a concentration of 2,000-4,000 ppm. Preferably, the final concentration of sulfuric acid is to be 25,000 ppm.

In step b), the filtrate (12) which is pH-adjusted and decolorized is introduced into the dilution tank of an electrodialysis device (3), and then desalted until the conductivity of an organic material (14) reaches 1,500 uS/cm or less, and preferably 1,000 uS/cm or less.

The desalted organic material (14) is sent to a concentrator (4) and it is concentrated to a sugar concentration of 50-70 Bx. Then, the resulting concentrate (15) is vacuum-crystallized or cold-crystallized by a direct recovery process, thereby producing xylose. The direct recovery process may be carried out in three stages (5, 6 and 7).

Hereinafter, the present invention will be described in further detail with reference to examples, but the scope of the present invention is not limited to these examples.

EXAMPLE

Example 1

Preparation of Sulfuric Acid Hydrolysate

Coconut shell, palm shell or an oil palm empty fruit bunch (OPEFB) was ground to be a mean area or 0.5-5.0 cm$^2$ or a mean length of 0.1-5.0 cm, and then dried at a temperature of 40-80° C. for 12-24 hours.

2,000-50,000 ppm of sulfuric acid is added to 100 g of dried coconut shell, palm shell or oil palm empty fruit bunch (PPEFB), acid hydrolysis was performed at a reaction temperature of 100-200° C., reaction pressure of 0-10 kgf/cm$^2$ for 0.5-10 hours, wherein the mixture ratio of acid hydrolysis solvent and biomass is 1:1-1:20.

TABLE 1

Measurement results of sugar concentration of xylose and conductivity in the hydrolysates

| | Coconut shell | Palm shell | OPEFB |
|---|---|---|---|
| Sugar contents ratio of Xylose (%) | 95.2 | 94.8 | 96.1 |
| Conductivity (uS/cm) | 45,000 | 48,000 | 43,000 |

Example 2

Production of High-Concentration Xylose by Countercurrent Extraction

The simplest extraction method is a repeated extraction with a pure solvent. However, in the present invention, countercurrent extraction was carried out in order to maximize soluble components from a raw material while obtaining a high-concentration extract.

Figure 3:
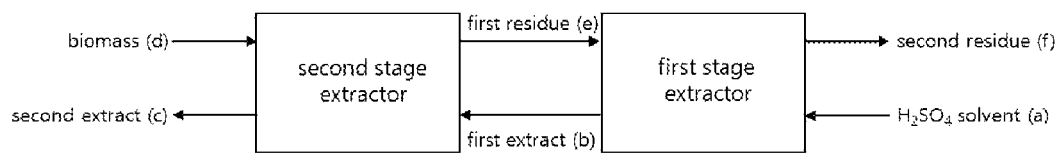
FIG. 3 shows a detailed flowchart of a multistage countercurrent extraction which is used in the present invention.
Figure 4:
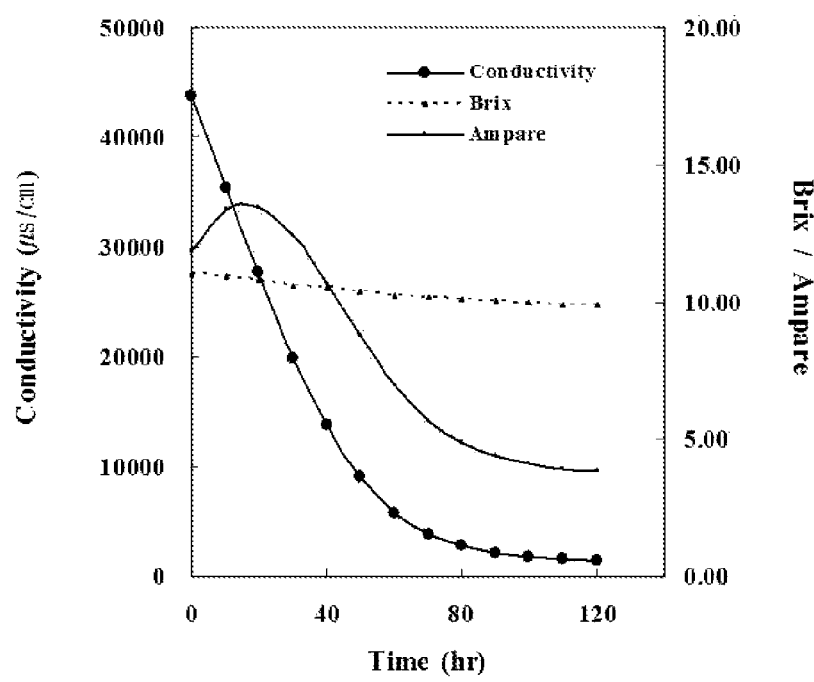
FIG. 4 shows the change in electrical conductivity over time in an electrolysis device which is used in the present invention.

When tropical fruit biomass and a sulfuric acid solution are allowed to react in an extractor for a predetermined time, they are separated into upper layer solution and lower layer slurry, which gradually move in opposite directions. In other words, a first extract (b) and a second extract (c), which consist of the solvent and the solute, moves in order through each column in a direction opposite to the solid phase, and during movement through each column, the solute is dissolved and extracted. FIG. 3 shows a flowchart of the countercurrent extraction process.

Specifically, the extractor consists of a stage-1 and a stage-2 extraction reactor. the continuous countercurrent extraction process comprises the steps of: transferring a low-concentration first extract from the stage-1 (b) having a xylose concentration of 3-7 Brix, to the stage-2 reactor; and passing the first extract (b) through the stage-2 extraction reactor to obtain a high-concentration and high-purity extract (c) having a xylose concentration of 10-20 Brix.

Under the conditions described in Example 1, the extraction yields of simple batch extraction (that is a repeated extraction with a pure solvent) and multistage countercurrent extraction were compared with each other. The multistage countercurrent extraction showed a high extraction yield of 90-80%.

TABLE 2

Comparison in extraction yield between simple batch extraction and multistage countercurrent extraction

| | Extraction yield (%) | Biomass hemicelluloses content (%) |
|---|---|---|
| Batch extraction | 60-70 | 15-30 |
| Multistage countercurrent extraction | 90-80 | |

The acid hydrolysate (c) having a pH of 0.8-1.2, obtained by the countercurrent extraction, was adjusted to a pH of 1.5-2.5 with sodium hydroxide and then decolorized with activated carbon and passed through a filter press having a pore size of 0.5 μm so as to remove suspended material.

Example 3

Desalting Electrodialysis

Current efficiency and energy consumption of the acid hydrolysate produced by the countercurrent extraction process were examined in order to determine the possibility of separation between an organic material (sugar) and sulfuric acid conducted by desalting electrodialysis process of the present invention by means of the desalting rate of sulfuric acid and the loss rate of the organic material.

The decolorized and filtered reaction solution had a sugar concentration of 10-15 Brix and a pH of 1.5-2.5. The solution was maintained at a constant voltage of 40-70V using a DC power supply (120V, 30 A) and at a constant temperature of about 40-70° C. using a heat exchange coil. The solution was desalted at a flow rate of 6-8 L/min for 100-150 minutes until the conductivity reached 1,500 uS/cm or less.

Herein, the electrodialysis device has three compartments and the ion membrane was comprised of a strong acid cation exchange membrane and a strong basic anion exchange membrane and had a total effective membrane area of 0.6 $m^2$. The results of the desalting electrodialysis are shown in Table 3 below.

TABLE 3

Results of desalting electrodialysis

| Desalting time (min) | Conductivity (uS/cm) | | Sugar concentration (Brix) | | Current efficiency (%) | Energy consumption (kWh/kg sugar) |
|---|---|---|---|---|---|---|
| | Diluent tank | Concentration tank | Diluent tank | Concentration tank | | |
| 0 | 50,000 | 200 | 15.0 | 0 | — | — |
| 120 | 1,000 | 48,000 | 14.5 | 0.5 | 95 | 0.2 |

The desalting rate of sulfuric acid can be calculated from the conductivity value of the diluent tank, and the loss rate of the organic material can be determined from a change in the Brix value of the diluent tank.

Desalting rate of sulfuric acid=100−{(final conductivity value/initial conductivity value)*100}

Loss rate of organic material=100−{(final Brix value/initial Brix value)*100}

As a result, the desalting rate of sulfuric acid was 98%, and the loss rate of the organic material (sugar) was 3.4%.

Example 4

Measurement of Contamination Index of Ion Exchange Membrane

Under the conditions described in Example 3, the ion exchange capacity and performance of the membrane were measured as a function of the pH of the acid hydrolysate. As a result, at a pH of 1.5-2.5, decline in the ion exchange capacity and performance of the membrane was significantly low, indicating that the membrane was not substantially contaminated. The results of the measurement are shown in Table 4 below.

TABLE 4

Contamination index of membrane

| | Ion exchange capacity (L) of membrane | Ion exchange performance (L/$m^2$-hr) of membrane |
|---|---|---|
| pH of 0.8-1.2 (raw extract) | 60 | 8 |
| pH of 1.5-2.5 | 300 or more | 30 |

Example 5

Recycling of Recovered Sulfuric Acid

In order to examine the possibility and economic efficiency of recycling of sulfuric acid recovered from the electrodialysis process, the extraction yield of xylose was measured when the recovered sulfuric acid was reused in the extraction process.

As a result, as can be seen in Table 5 below, the extraction yield obtained when using only the recovered sulfuric acid was 10.61%, and the extraction yield obtained when using a mixture of sulfuric acid and the recovered sulfuric acid was 12.80% similar to that of the control. Table 5 below shows the extraction yield obtained when adding a minimum amount of sulfuric acid to the recovered sulfuric acid and reusing the mixture. The average yield of a total of six extraction experiments in which the recovered sulfuric acid was repeatedly reused was 12.57% as shown in Table 6 below. This suggests that the recovered sulfuric acid can be repeatedly used.

TABLE 5

Effect of addition of recovered sulfuric acid and sulfuric acid on extraction yield

| | Sulfuric acid concentration | | | Recovery rate of sulfuric acid |
|---|---|---|---|---|
| | Recovered sulfuric acid (ppm) | Sulfuric acid (ppm) | Extraction yield (%) | |
| Control | 0 | 25,000 | 12.04 | 0 |
| Example 1 | 22,000 | 0 | 10.61 | 88 |
| Example 2 | 22,000 | 3,000 | 12.80 | 88 |

TABLE 6

Results of repeated use of recovered sulfuric acid in hydrolysis

| | Sulfuric acid concentration | | Extraction yield (%) | Recovery rate of sulfuric acid (%) |
|---|---|---|---|---|
| | Recovered sulfuric acid (ppm) | Sulfuric acid (ppm) | | |
| Reuse 1 | 22,000 | 3,000 | 12.80 | 88 |
| Reuse 2 | 21,750 | 3,250 | 12.80 | 87 |
| Reuse 3 | 21,750 | 3,250 | 12.71 | 87 |

TABLE 6-continued

Results of repeated use of recovered sulfuric acid in hydrolysis

| | Sulfuric acid concentration | | | Recovery |
|---|---|---|---|---|
| | Recovered sulfuric acid (ppm) | Sulfuric acid (ppm) | Extraction yield (%) | rate of sulfuric acid (%) |
| Reuse 4 | 22,250 | 2,750 | 12.32 | 89 |
| Reuse 5 | 21,500 | 3,500 | 12.79 | 86 |
| Reuse 6 | 21,750 | 3,250 | 12.04 | 87 |

Example 6

Recovery of Xylose by Direct Recovery Process

In order to examine the rate of direct recovery of the desalted organic material from the electrodialysis process, the recovered organic material was concentrated such that the sugar concentration was increased from 10-15 Brix to 50-70 Brix. Xylose was recovered from the concentrated organic material by a 3-step direct recovery process while the recovery rate of xylose was measured.

As a result, as shown in Table 7 below, the recovery rate of xylose (5, 6 and 7 in FIG. 2) was 33.5%, and the total recovery rate of xylose obtained when recovering and recrystallizing the second and third crystal solutions (16 and 17 in FIG. 2) was 87% similar to the xylose recovery rate of the prior art process comprising an ion purification process.

TABLE 7

| Direct recovery process | Recovery rate of xylose (%) | Purity of xylose (%) | Sugar composition of separated mixed hydrolysates | | | |
|---|---|---|---|---|---|---|
| | | | Xylose | Glucose | Glactose | Arabinose |
| DR_1 Step | 87 | 95 | 70 | 7 | 6 | 17 |
| DR_2 Step | 70 | 98 | 92 | — | — | 8 |
| DR_3 Step | 55 | 99 | 99 | — | — | — |

The invention claimed is:

1. A process for producing xylose by hydrolyzing tropical fruit biomass with sulfuric acid, the process comprising the steps of:
    a) countercurrently extracting tropical fruit biomass by hydrolysis with sulfuric acid to obtain an extract;
    b) adjusting the extract to a pH of 1.5-2.5 and decolorizing and filtering the pH-adjusted extract to obtain a filtrate;
    c) desalting the filtrate in an electrodialysis device; and
    d) recycling a waste sulfuric acid solution recovered from step c), to step a), and concentrating and directly recovering the desalted organic material to obtain xylose crystals, wherein the process does not comprise a step of precipitation, neutralization and ion-exchange.

2. The process of claim 1, wherein 2,000-4,000 ppm of sulfuric acid is added to the waste sulfuric acid solution recovered from step c) before the recovered waste sulfuric acid solution is recycled to step a).

3. The process of claim 1, wherein the xylose concentration of the filtrate in step b) is 80% or more.

4. The process of claim 1, wherein the filtrate in step c) is desalted until the filtrate reaches a conductivity of 1,000 uS/cm or less.

5. The process of claim 1, wherein the sugar content ratio of the extract in step a) is 60-90% based on the weight of the separated mixed hydrolysates.

* * * * *